US006743429B2

(12) United States Patent
Cadieux

(10) Patent No.: US 6,743,429 B2
(45) Date of Patent: Jun. 1, 2004

(54) USE OF CALCITONIN GENE-RELATED PEPTIDE IN THE PREVENTION AND ALLEVIATION OF ASTHMA AND RELATED BRONCHOSPASTIC PULMONARY DISEASES

(75) Inventor: Alain Cadieux, Rock Forest (CA)

(73) Assignee: Sherbrooke University, Quebec (CA)

( * ) Notice: Subject to any disclaimer, the term of this patent is extended or adjusted under 35 U.S.C. 154(b) by 36 days.

(21) Appl. No.: 09/475,072

(22) Filed: Dec. 30, 1999

(65) Prior Publication Data

US 2002/0037846 A1 Mar. 28, 2002

(30) Foreign Application Priority Data

Dec. 24, 1999 (CA) .............................................. 2292902

(51) Int. Cl.$^7$ ............................................... A61K 39/00
(52) U.S. Cl. ........................ 424/198.1; 514/12; 514/826
(58) Field of Search .................. 514/12, 826; 424/198.1

(56) References Cited

U.S. PATENT DOCUMENTS

| | | | |
|---|---|---|---|
| 4,530,838 A | 7/1985 | Evans et al. .................... 514/11 |
| 4,549,986 A | 10/1985 | Evans et al. ........... 260/112.5 T |
| 4,687,839 A | 8/1987 | Kempe ......................... 530/324 |
| 4,697,002 A | 9/1987 | Kempe ......................... 530/324 |
| 4,736,023 A | 4/1988 | Evans et al. ................... 536/27 |
| 4,992,530 A | 2/1991 | Morita et al. ................ 530/307 |
| 5,049,654 A | 9/1991 | Morita et al. ................ 530/307 |
| 5,510,339 A | * 4/1996 | Gleich et al. |
| 5,569,604 A | 10/1996 | Russo et al. |
| 5,622,839 A | 4/1997 | Moore et al. |
| 5,710,024 A | 1/1998 | Adamou et al. ............ 435/69.1 |
| 5,858,978 A | * 1/1999 | Vignery |

OTHER PUBLICATIONS

Rosenwasser. L. J. Allergy Clin. Immunology, 102:344–350, 1998.*
Skolnick, et al., Trends in Biotech., 18(1):34–39, Jan. 2000.*
Merck Manual, Beers and Berkow, Eds., Merck Research Laboratories, Whitehouse Station, NJ, 1999.*
Barnes et al.; "Neuropeptides in the Respiratory Tract"; AM Rev. Respir. Dis.; vol. 144; 1991; pp. 1391–1399.
Lundberg et al.; "Co–Existence of Substance P and Calcitonin Gene–Related Peptide–Like Immunoreactivities in Sensory Nerves in Relation to Cardiovascular and Bronchoconstrictor Effects of Capsaicin"; European Journal of Pharmacology; vol. 108; 1985; pp. 315–319.
Martling et al.; "Calcitonin Gene–related Peptide and the Lung: Neuronal Coexistence with Substance P, Release by Capsaicin and Vasodilatory Effect"; Regulatory Peptides; vol. 20; 1988; pp. 125–139.
Cadieux et al.; "Carbamylcholine–and 5–hydroxytryptamine–induced Contraction in Rat Isolated Airways: Inhibition by Calcitonin Gene–related Peptide"; Br. J. Pharmacol.; vol. 101; 1990; pp. 193–199.

Luts et al.; "Neuropeptides in Guinea Pig Trachea; Distribution and Evidence for the Release of CGRP into Tracheal Lumen"; Peptides; vol. 11; 1990; pp. 1211–1216.
Bhogal et al.; "The Effects of IAPP and CGRP on Guinea Pig Tracheal Smooth Muscle in Vitro"; Peptides; vol. 15, No. 7; 1994; pp. 1243–1247.
Pinto et al.; "Effects of Adrenomedullin and Calcitonin Gene–related Peptide on Airway and Pulmonary Vascular Smooth Muscle in Guinea–Pigs"; British Journal of Pharmacology; vol. 119; 1996; pp. 1477–1483.
Hamel et al.; "Contractile Activity of Calcitonin Gene–related Peptide on Pulmonary Tissues"; J. Pharm. Pharmacol; vol. 40; 1988; pp. 210–211.
Tschirhart et al.; "Evidence for the Involvement of Calcitonin Gene–related Peptide in the Epithelium–dependent Contraction of Guinea–pig Trachea in Response to Capsaicin"; Naunyn–Schmied. Arch. Pharmacol; vol. 342; 1990; pp. 177–181.
Gatto et al.; "Calcitonin and CGRP Block Bombesin– and Substance P –induced Increases in Airway Tone"; J. Appl. Physiol.; vol. 66; 1989; pp. 573–577.
Kanazawa et al.; "Calcitonin Gene–related Peptide Antagonizes The Protective Effect of Adrenomedullin on Histamine–Induced Bronchoconstriction"; Clinical and Experimental Pharmacology and Physiology; vol. 23; 1996; 472–475.
Nagase et al.; "roles of Calcitonin Gene–Related Peptide (CGRP) in Hyperpnea–induced Constriction in Guinea Pigs"; Am. J. Respir. Crit. Care Med.; vol. 154; 1996; pp. 1551–1556.
Kroll et al.; "Capsaicin–induced Bronchoconstriction and Neuropeptide Release in Guinea Pig Perfused Lungs"; J. Appl. Physiol.; vol. 68; 1990; pp. 1679–1687.
Kanemura et al.; "Calcitonin Gene–related Peptide Augments Parasympathetic Contraction of Rabbit Tracheal Smooth Muscle in vitro"; Agents and Actions; vol. 31; 1990; pp. 219–224.
Kannan et al.; "Functional Innervation of Pig Tracheal Smooth Muscle: Neural and Non–Neural Mechanisms of Relaxation"; The Journal of Pharmacology and Experimental Therapeutics; vol. 260, No. 3; pp.; 219–224.
Martling et al.; "Innervation of Lower Airways and Neuropeptide Effects on Bronchial and Vascular Tone in the Pig"; Cell Tissue Res.; vol. 260; 1990; pp. 223–233.
Manzini; "Bronchodilation by Techykinins and Capsaicin in the Mouse Main Brochus"; Br. J. Pharmacol: vol. 105; 1992; pp. 968–972.

(List continued on next page.)

Primary Examiner—Patrick J. Nolan
(74) Attorney, Agent, or Firm—Foley & Lardner

(57) ABSTRACT

The present invention relates to the use of calcitonin gene-related peptide (CGRP) in the prevention and alleviation of asthmatic symptoms. In contrast to other therapeutic agents now in use, CGRP combines both bronchoprotector and anti-inflammatory properties. Furthermore, it prevents both early and late phase bronchial responses associated with an asthma attack and its effective dose is small enough that undesirable haemodynamic side effects are not present.

13 Claims, 10 Drawing Sheets

OTHER PUBLICATIONS

Parsons et al.; "Peptide Mediator Effects on Bronchial Blood Velocity and Lung resistance in Conscious Sheep"; J. Appl. Physiol; vol. 72; pp. 1118–1122.

Ninomiya et al.; "The Effects of Calcitonin Gene–related Peptide on Tracheal Smooth Muscle of Guinea–Pigs in vitro"; British Journal of Pharmacology; vol. 119; 1996; pp. 1341–1346.

Cadieux et al.; "Bronchoprotector Properties of Calcitonin Gene–related Peptide in Guinea Pig an Human Airways"; Am. J. Respir. Crit. Care Med.; vol. 159; 1999; pp. 235–243.

Cadieux et al.; "Inhibitory Effects of Calcitonin Gene–related Peptide (CGRP) on Contraction of Smooth Muscles of the Rat Airways"; 1988; p. A60.

Cadieux et al.; "Inhibition by Calcitonin Gene–related Peptide of Agonist–Induced Bronchcostriction in Various Mammals Including Man"; Agent and Actions; vol. 31; 1990; pp. 211–214.

Lanoue et al.; "Characterization of CGRP Receptor Sited in Rat Airways"; Ann. N.Y. Acad. Sci.; vol. 657; 1991; pp. 441–444.

* cited by examiner (A) Bronchus (B) Parenchyma

A

B

USE OF CALCITONIN GENE-RELATED PEPTIDE IN THE PREVENTION AND ALLEVIATION OF ASTHMA AND RELATED BRONCHOSPASTIC PULMONARY DISEASES

FIELD OF THE INVENTION

The present invention teaches that calcitonin gene-related peptide (CGRP), a neurotransmitter present in sensory nerves of several mammalian species, including humans, displays potent and efficient bronchoprotector and anti-inflammatory properties. More specifically, the present invention discloses that CGRP, when administered by inhalation to mammals, is capable of reducing the accumulation of eosinophils in the bronchial walls and of preventing bronchospastic airway responses, especially reversible airway hyperreactivity such as that encountered in bronchial asthma.

BACKGROUND OF THE INVENTION

Bronchial asthma may be defined as a clinical syndrome characterized by outbursts of suffocation and of severe discomfort, especially when air is exhaled from the lungs. These asthma outbursts or asthma attacks often occur after exertions or during the night, are reversible either spontaneously or following treatments and are generally the result of bronchial obstructions. Three major factors contribute to these obstructions: a spasm (contraction) of the smooth muscles surrounding the airways, an inflammation of the bronchial walls accompanied by an effusion of fluid (oedema) and an hypersecretion of mucus. Although the relative contribution of each of these conditions is unknown, the net result is an increase in airway resistance, hyperinflation of the lungs and thorax, as well as abnormal distribution of ventilation and pulmonary blood flow. Thus, when an asthma attack occurs, breathing becomes difficult and may be accompanied by wheezing, coughing and dyspnea.

A major feature of this disorder is the propensity of the airways of asthmatics to respond in an abnormally exaggerated way (bronchial hyperreactivity) to a large variety of apparently unrelated stimuli such as allergic triggers, cigarette smoke, dust, pollens, chemical products, irritating vapours, cold air, food substances, physical exertion, stress, etc. Because of this increase in the sensitivity of the airways (10 to 1000 times normal), asthma has for a long time been regarded as a disease of the large airways which was believed to be caused mainly by mucus secretion and extensive narrowing of the tracheobronchi which consequently made breathing difficult for asthmatics.

This view started to change when morphometric studies on the bronchi of asthmatics revealed the presence of major inflammatory reactions within the mucosa of the bronchi. It is now recognized that another hallmark of this pathology is the massive influx of inflammatory cells, particularly eosinophils, in the bronchial walls and lung parenchyma. These cells are attracted to the airway mucosa by sequential processes involving adhesion molecules and a subset of helper T-lymphocytes designated Th2 that secrete an array of cytokines and chemokines. Eosinophils, for which the survival time is prolonged by these same cytokines, remain in the bronchial mucosa and release, among others, cysteinyl leukotriens, several hydrolytic enzymes, toxic mediators such as eosinophilic cationic protein and TNFα as well as Th2 cytokines, all of which cause further tightening of the airway smooth muscles cells and increased inflammatory reaction including increased eosinophilia. The importance of pulmonary inflammation to asthmatic response has been appreciated only recently but it is now well accepted that this inflammation paves the way for non-specific hyperresponsiveness and worsens airway obstruction.

Several subtypes of asthma have been identified during the last few years and it is estimated that in its different forms (i.e. allergic asthma and idiosyncratic asthma), this disease affects approximately 8 to 10% of the world's general population, of which 5 to 10% are children.

If asthma attacks are mild, patients can take a medication (generally a bronchodilator) to suppress spasms (contractions) of the bronchi. If, however, attacks are severe and/or frequent, steroids can be added to the bronchodilator in order to reduce the inflammation occuring in the lungs. There are currently five types of remedies available on the market to treat asthma: (1) aerosol dosers (inhalators) which dispense bronchodilators, or agents that cause the relaxation of the bronchi (such as β2-adrenergic agonists administered with tiny delivery systems); (2) methylxanthines (such as theophylline), which are bronchodilators in tablet or capsule form; (3) corticosteroids (such as fluticasone or budenoside), used to reduce inflammation, available in aerosol, liquid or tablet form; (4) inhibitors of mast cell degranulation (i.e. chromones such as cromolyn sodium), most often used to prevent asthma triggered by physical activities, available either in tablet or aerosol form; and (5) antagonists of leukotrienes $D_4$ and $E_4$ (such as zafirlukast and montelukast), used as prophylactic substitutes to aerosol dosers, available in tablet form.

None of the medicines currently in use combines both bronchoprotector and anti-inflammatory properties. Additionally, none constitutes a cure for asthma, but each medicament can control its symptoms to varying degrees depending on the patient and/or the severity of his or her affliction. As a common feature, these medicines are comprised of synthetic or modified molecules and consequently, most cause secondary, undesirable effects, either at the moment of administration or following prolonged usage. For example, some β2-adrenergic agonists can bring about hand tremors, tachycardia and hypotension. Theophylline can induce nausea, diarrhea, headaches, muscle cramps, irritability, etc. Inhaling corticosteroids can irritate the vocal cords, resulting in hoarseness, as well as interfere with adrenal gland activity. They also induce several systemic effects such as elevated blood sugar, rounding of the face, changes in mood, high blood pressure, etc.

In view of the clinical importance of asthma, there is clearly an urgent need to identify new factors which can play a role in preventing, alleviating or correcting disfunctions such as inflammation and bronchial hyperactivity, such as those encountered in bronchial asthma. Thus, it is a feature of the present invention to prevent, reduce and/or alleviate the pathophysiological manifestations of asthma by the administration of a new and natural compound which combines both bronchoprotector and anti-inflammatory properties and which also has less undesirable side effects than those induced by the medicines now in use. It is another feature of the present invention to provide a method for the reduction and/or alleviation of the symptoms of asthma, by the use of a new therapeutic tool (i.e. CGRP) which is rapid acting and of relatively long duration.

Calcitonin gene-related peptide (CGRP) is a mammalian peptide containing 37 amino acid residues with a disulphide bridge between (Cys2 and Cys7. It is generated by tissue-specific RNA processing of the primary transcript of the calcitonin gene and is expressed mainly in thyroid parafollicular cells as well as in nuclei and nerve fibers of the central and peripheral nervous systems. In humans as in rats, this peptide is known to occur in two highly homologous forms, designated α- and β-CGRP, which differ in their primary sequence by one and three amino acids, respectively.

CGRP is widely distributed in the lung innervation of several mammalian species including humans. Peripheral branches of CGRP-containing nerve fibers are located beneath and within the airway epithelium, around blood vessels and seromucous glands, and within the smooth muscle layers of the tracheo-bronchial tree. Co-stored with substance P (SP) and neurokinin A (NKA) in primary afferent sensory neurons, CGRP is released (together with SP and NKA) from nerve endings upon capsaicin stimulation and after exposure to chemical irritants. Although the possible roles of this neurotransmitter in lung physiological and pathological processes are unknown, its production in the vicinity of bronchial smooth muscle cells led several investigators to suggest that CGRP could also affect (as do SP and NKA) adjacent tracheobronchial tone.

Numerous in vitro and in vivo investigations have been carried out with the aim of determining the role of CGRP on tracheobronchial smooth muscle cells. Although several of these studies have, to a large extent, focused on the putative myotropic activity of CGRP (i.e. contractile- or relaxant-induced responses), its main effect on airway smooth muscle tone still remains unclear, as considerable controversial data have been reported. For example, in human isolated airways, evidence has been provided for (1) and against (3) a bronchoconstrictor action of CGRP. Similarly, Luts and coworkers (5), Bhogal and coworkers (6), and Pinto and coworkers (7) showed that CGRP does not exert any contractile or relaxant effect in guinea pig trachea, whereas Hamel and Ford-Hutchinson (8) and Tschirhart and coworkers (9) reported that CGRP is one of the most potent contractile agents on guinea pig trachea yet identified. On the other hand, CGRP has been found to have no effect on hilus bronchi and parenchyma in the guinea pig in vitro (3, 7, 8) and to cause no changes in airway resistance in guinea pig in vivo (2, 3, 10–12).

More recently CGRP has been reported to potentiate the cholinergic contractions elicited by electrical field stimulation (EFS) in guinea pig trachea (7), to produce no bronchoconstriction in isolated and perfused guinea pig lung (13), to induce relaxations in guinea pig trachea precontracted with KCl and prostagiandin $F_{2\alpha}$ ($PGF_{2\alpha}$) (6), but to be without any relaxant effect in human and guinea pig bronchi precontracted with NKA (3) and in guinea pig trachea precontracted with histamine (7). In other animal species, CGRP has been shown to have no contractile effect on the airway smooth muscle in the rabbit (14), pig (15, 16), rat (4, 8), and mouse (17) in vitro and in sheep in vivo (18). Finally, CGRP has been noted to cause relaxations in pig trachea (15) and bronchi (16) precontracted with carbamylcholine and histamine, respectively, and in mouse airways precontracted with carbachol (17). Given this wide spectrum of reported pharmacological activities for CGRP, it may be easily understood that no investigator has really succeeded in ascribing a specific role for this neuropeptide with regard to its involvement in the regulation of airway smooth muscle tone. This issue has been in debate for some time in the scientific literature. Because no concensus has been reached yet, it is generally suggested that either the pharmacological effect of CGRP greatly differs between animal species and different levels of the tracheobronchial tree or that this sensory neuropeptide is related to pulmonary physiological processes other than those involved in the regulation of bronchomotor tone.

SUMMARY OF THE INVENTION

The present invention relates to the use of calcitonin gene-related peptide (CGRP) in the prevention, reduction and/or alleviation of the pathophysiological manifestations of asthma. The invention further concerns the use of active molecules (such as members of the calcitonin family of peptides i.e. CGRP, adrenomedullin, amylin, calcitonin and/or their respective functional derivatives; analogs and fragments) that are able to bind to the receptors that activate the intra and/or intercellular signaling pathways that mediate either or both the anti-inflammatory and bronchoprotective effects of CGRP in the lung.

The invention additionally pertains to an improved method for preventing or controlling ailments encountered in asthma (i.e. bronchial hyperreactivity and inflammation) which comprises administering to the host suffering therefrom an effective therapeutic amount of CGRP. The invention also provides improved means for preventing, alleviating and/or reducing bronchospastic airway responses characterized by reversible airway hyperreactivity by administering an amount of CGRP (or of its natural homologs and/or of their respective functional derivatives) sufficient to reduce airway hyperreactivity. In accordance with the foregoing, the invention also proposes a mode of administration having properties superior to those of other medications, especially superior properties in terms of bronchoprotection and anti-inflammation, and with less secondary side effects.

CGRP is produced in the lung and is released during asthma attacks. We found that it prevents mucosal inflammation and constriction of the tracheobronchial tree in a natural way (see Examples, below). CGRP is therefore a natural substance present in mammalian species (including man), and one of its primary functions at the level of the respiratory tract is to exert a protective effect on the airways and, more specifically, to reduce the intensity of the bronchospasms induced by an asthma crisis. Other advantages attributable to CGRP are that it exercises a non-specific bronchoprotector effect, it does not cause undesirable haemodynamic side effects when administered by inhalation and that it also acts as an anti-inflammatory agent in the lung. CGRP is thus a molecule that highly surpasses everything in the arsenal of therapeutic agents currently available to prevent and attenuate ailments and symptoms associated with asthma.

These and other objects, features and many of the attendant advantages of the invention will be better understood upon a reading of the following detailed description of the invention when considered with the accompanying drawings.

DETAILED DESCRIPTION OF THE INVENTION

Figure 1:
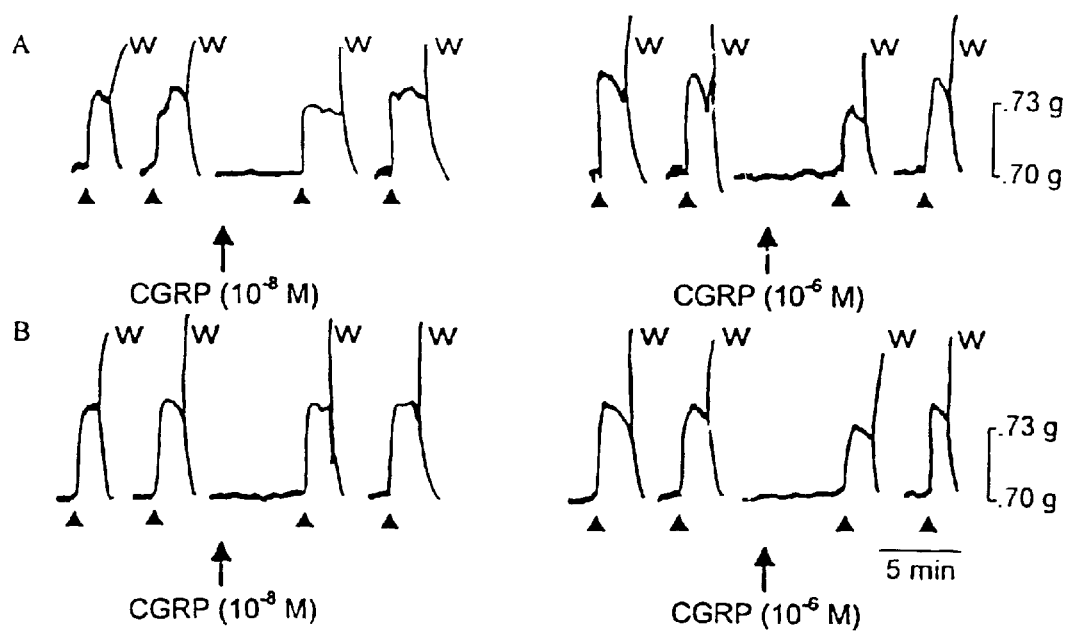
FIG. 1 shows the inhibitory effect of CGRP on contractions evoked by $5 \times 10^{-8}M$ substance P (SP) in isolated parenchymal strips from (A) control and (B) ovalbumin (OA)-sensitized guinea pigs. Contractions were elicited by SP (triangles) at 15 min intervals in the absence or in the presence of various concentrations of CGRP. Note that the inhibitory action of CGRP is more pronounced in tissues from non-sensitized animals. Ordinate scale: changes of tension in g. Abscissa scale: time in min. W=washouts.

The present invention concerns control and prevention of bronchospastic airway diseases, especially reversible airway hyperreactivity and lung inflammation such as those encountered in asthma, by administration of the neuropeptide CGRP.

We recently analysed in greater detail the available data reporting the effects of CGRP (20), and we found that they are not as conflicting as they might first appear to be. For example, regardless of the origin of the airway preparation used (animal species and level of the tracheobronchial tree), most studies examining the effect of CGRP on the baseline tension of the airway smooth muscles resulted in identical data, as no contractile or relaxant response was observed (3, 4, 5–8, 11, 12, 14, 15, 17). In studies showing a contractile action for CGRP (for example, in guinea pig trachea), there is a consensus regarding the epithelium dependency for this effect of the peptide but the magnitude of the response evoked by CGRP was each time described as being weak and of minor importance: 30% of the maximum induced with $1.5\times10^{-5}$ M of methacholine (8), 14% of the capsaicin ($10^{-5}$ M) maximum (9), and 8% of 50 mM KCl-induced contraction (19). Thus, when compared with SP and NKA, which are well recognized potent bronchoconstrictor agents (5), the data so far accumulated on the pharmacological effects of CGRP do not really speak in favor of an efficient and potent constrictor activity for this sensory neuropeptide in airway smooth muscle. On the contrary all the data yet accumulated using isolated airways, point to an absence of myotropic activity for CGRP. To that effect, it is worthy of note that in all experiments measuring pulmonary resistance in vivo, no bronchoconstriction or bronchodilation was detected in guinea pigs (2, 3, 10–12) and sheep (18) in which CGRP was administered intravenously.

From the studies reporting a bronchodilatory effect with CGRP, a similar statement of fact can be made, as the relaxations evoked by CGRP were characterized as being weak (15, 16), modest (6), very small and even erratic (17). Thus from the data yet available, it would appear a bit premature and probably too strong a statement to claim that CGRP has to be regarded as a potent and efficient bronchodilatory agent. The results of our analysis speak strongly for an absence of significant myotropic activity. Similar conclusions have been put forward by various investigators so that it is now generally reported that CGRP does not exert any significant pharmacological or physiological myotropic effect in airway smooth muscle and that this peptide is not involved whatsoever in the regulation of the tracheobronchial smooth muscle tone.

A few years ago, we also attempted (as did many other investigators) to determine whether CGRP had any pharmacological effect on the smooth muscle of rat isolated airways (4, 21). We found that in this animal species, CGRP was devoid of any direct contractile or relaxant effects in all airway preparations tested (i.e. trachea, bronchi and lung parenchymal strips). This would be in keeping with numerous observations made by several other groups of investigators, as discussed previously. Interestingly, however, we also found that behind this apparent lack of pharmacological activity, CGRP presented a marked ability to prevent, in a concentration-related manner, bronchospasms induced by carbamylcholine and 5-hydroxytryptamine. This indicates that in rats, CGRP might act as a modulatory agent rather than a direct agonistic compound (i.e. contraction or relaxation) and that its inhibitory effect could be directed against different contractile substances belonging to chemically distinct families. Another interesting finding from our investigation was that the bronchoprotector effect of CGRP was more powerfully expressed in distal than in proximal airways, suggesting that CGRP might be of functional importance mainly in the periphery of the tracheobronchial tree (4).

Recently, we re-examined this inhibitory effect of CGRP with the aim of determining whether this peptide was also capable of exerting its bronchoprotector effect in airways obtained from different mammalian species. As it is revealed in the present document, we found that CGRP behaves as a potent bronchoprotector agent not only in isolated airways (guinea pig and human) but also following intravenous (guinea pig) and aerosol (sheep) administration. Thus, in contrast to the conflicting data currently reported on the myotropic effect of CGRP, the results of our investigations suggest that there are not interspecies variations in this newly discovered property of CGRP to act as a bronchoprotector agent in mammalian airways.

In order to further define its potential role in asthma, measurements of plasma levels of CGRP were made before and after an allergen challenge (ovalbumin) both in normal and in allergic asthmatic guinea pigs. While the plasma levels were unchanged in normal animals, asthmatic guinea pigs showed a significant increase in the concentration of circulating CGRP, which occurred within the first 20 minutes following allergen provocation (unpublished data). Similar observations were thereafter noted in asthmatic patients; we observed that plasma levels of CGRP were significantly higher in subjects during periods of exacerbations of asthma than in control subjects or in patients having asthma under control (unpublished data). Finally, we have also accumulated data which show that administration in guinea pigs of a CGRP receptor antagonist, namely hCGRP$_{(8-37)}$, 5 minutes before the allergen challenge, resulted in a significant increase in the magnitude of the allergen-induced bronchospasm when compared to that observed in animals untreated with hCGRP$_{(8-37)}$. These observations confirm that CGRP is effectively released during an asthma attack and that it does participate in the neuromodulation of bronchomotor tone. We thus hypothesized that CGRP is significantly involved in the control of airway smooth muscle tone during an asthma attack and that one of its natural functions is to exert a protective effect against the contractile agents produced during the asthma crisis.

Thus, the bronchoprotector properties of CGRP, which has now been discovered from basic pharmacological research work on pulmonary physiology is new and was unexpected from a knowledge of the state of the art. This peptide, due to its ability to exert a powerful and non-specific bronchoprotector effect, could be particularly useful as a natural anti-asthmatic agent. Because asthma symptoms are the net result of two major determinants, namely airway hyperresponsiveness and airway inflammation, novel substances capable of exerting bronchoprotecor effects in addition to suppressing and/or reducing airway inflammation are desired when aiming to achieve asthma control. Accordingly, it is an object of the present invention to provide novel means to prevent, reduce and/or alleviate the pathophysiological manifestations of asthma by using CGRP. In order to accomplish the above object, the potential anti-asthmatic effects of CGRP in various animal models of asthma were investigated both in vitro and in vivo. As a result of these investigations, we have found that CGRP, when administered by inhalation, combines both potent bronchoprotector and anti-inflammatory activities. (See Examples, below.) The present invention has been accomplished on the basis of these discoveries.

As used herein, "asthma" refers to either allergic or idiosyncratic asthma. An agent is said to have a therapeutic potential if it may lessen (i.e. attenuate) the severity, extent or duration of the asthma symptoms. Such agents are preferably identified through the use of the following "asthma model systems". As used herein, an agent is said to be able to prevent, alleviate or correct disfunctions such as the inflammation and bronchial hyperreactivity encountered in bronchial asthma if, when administered to a mammal, including humans, the agent is capable of attenuating either the severity, extent or duration of asthma symptoms. The term "reversible airway hyperreactivity" refers to conditions such as allergen, non-specific and exercise-induced asthma etc, which result in reversible blockage of the air passages. So-called irreversible airway conditions such as emphysema also involve reversible aspects. The term "lung inflammation" refers to eosinophil accumulation in airway tissue as well as eosinophil recruitment in bronchoalveolar lavage. As used herein, an agent is said to exert an anti-inflammatory effect if, when administered to a host, the agent is capable of reducing the population of eosinophils in bronchial walls concomitantly with increasing their recruitment in bronchoalveolar lavage, thereby reducing their stay in lung tissue and consequently their toxic and harmful effects. The present invention is most useful in the prevention and management of both acute and chronic conditions.

The term "CGRP" as used herein means a neuropeptide produced by stimulated mammalian sensory nerve fibers and neuroendocrine cells. This term is also intended to include any peptide which shares significant structural and functional homology with the calcitonin gene-related peptide set forth in the present invention i.e., functions as CGRP. CGRP homolog means any other natural peptide produced within the organism that is structurally related to CGRP (i.e., that shares similar amino acid sequences and that is classified into the same family). For example, the amino acid sequences of CGRP peptides are very well conserved (85–98% homology) among mammalian species and all CGRPs are members of the calcitonin family of peptides. This calcitonin family of peptides also includes the related peptide amylin (46% homology with CGRPs), salmon calcitonin (32% homology with CGRPs) and adrenomedullin (24% homology with CGRPs). All these peptides belonging to the calcitonin family of peptides have in general a N-terminal ring structure of 6–7 amino acids involving a disulfide bridge and an amidated C-terminal end. Because of these common structural features, all of them can cross-react to a varying extent with each other's receptors and induce the same effects. Examples of cross reaction between these peptides include, among others, regulation of cardiovascular homeostasis (CGRP, amylin, calcitonin, adrenomedullin), modulation of glycogen metabolism (amylin, calcitonin, CGRP) and production of hypocalcemic effects (calcitonin, CGRP, amylin). The essential functional aspect of these CGRP-like peptides in the context of the present invention is that when administered to a mammal, they might be capable of binding the receptors that are activated by CGRP and consequently to initiate similar bronchoprotector and anti-inflammatory effects.

In accordance with the foregoing, the invention also relates to analogs of these peptides. The term analog when referring to the peptide of the present invention means a peptide which retains and/or induces essentially the same biological functions i.e., bronchoprotector and anti-inflammatory effects of CGRP or 1°) retains the ability to bind and activate the CGRP receptor or any other receptor that may be involved in the bronchoprotector effect of CGRP and 2°) activates the mechanisms underlying the chemotaxis of inflammatory cells. By "analogs" is further meant a natural peptide (CGRP or its natural homologs: amylin, calcitonin and adrenomedullin) in which modifications have been made in order to make the peptide more resistant to enzymatic degradation and/or to increase its effectiveness to bind and activate the CGRP receptor responsible for the bronchoprotector effect and/or to trigger the chemoattractile mechanism for inflammatory cells. Modifications can occur anywhere in a polypeptide including the peptide backbone, (i.e. the amino acid sequence), the amino acid side chains and the amino or carboxyl termini. Among variants in this regard are, but are not limited to, variants that differ from the aforementioned peptide by amino acid substitutions, deletions or additions. These substitutions, deletions or additions may involve one or more amino acids. Such analogs may result when amino acids of a synthetically prepared peptide are deleted, added or replaced in such a manner as to yield a peptide having a similar function, i.e. that functions as an agonist to CGRP. For example, we have shown that the linear analog of CGRP, diacetoamidomethyl cysteine CGRP ([Cys(AC,M)$^{2,7}$] CGRP) can induce a brochoprotector effect similar to (although with less efficiency than) that of CGRP. Other variants also include modifications in the amino or carboxyl termini. In fact, blockade of the amino or carboxyl group in a polypeptide, or both, by a covalent modification, is common in naturally occurring and synthetic polypeptides and such modifications may be present in polypeptides of the present invention as well.

Also considered to be within the scope of the present invention are fragments and natural derivatives of these peptides (CGRP or its natural homologs; amylin, calcitonin and adrenomedullin). These include peptides that can be converted to biologically active peptides capable of activating the physiological mechanism underlying either or both the bronchoprotector and/or anti-inflammatory effects of CGRP. Active fragments of CGRP or of its natural homologs are peptides derived from CGRP or from its natural homologs, which have N-terminal, C-terminal, or both N-terminal and C-terminal amino acid residues deleted, but which retain the biological activity of CGRP as described herein. These fragments and/or derivatives may be prepared by enzymatic digestion of CGRP or of its natural homologs, or may be chemically synthesized or produced by genetic engineering procedures. They may also appear in the microenvironment as it occurs in nature following enzymatic degradation of the native peptides.

Although only certain embodiments of the invention have been described in specific detail (i.e. with regard to the fragments and derivatives of CGRP), which constitute the best mode presently known by the inventor, it should be understood that many other specific embodiments may be practiced and various changes and modifications as would be obvious to one having the ordinary skill in this art may be made without departing from the scope of the invention which is set forth in the claims appended hetero. For example, substitutions and modifications at specific positions in the CGRP peptide chain (or its natural homologs: amylin, calcitonin and adrenomedullin) can be made in accordance with present or future development without substantially detracting from potency and efficiency, and such peptides are considered as being within the scope of the invention. Even the common modifications that occur naturally in polypeptides, Which changes are too numerous to list exhaustively here, are also included. Such changes and modifications are well described in basic texts and in more detailed monographs, as well as in reams of research literature, and they are well known to those of skill in the art. "Pure" or "Purity", for purposes of this application, means that the modified peptide is present in substantially greater purity than it is found in any natural extract and that the composition is free from any biologically-active substances that would detract from its effectiveness. It also means that the modified peptide, regardless of any modification that has been practiced on it, is capable of mimicking or activating the intra and/or intercellular signaling pathways that are involved in either or both the bronchoprotector and anti-inflammatory effects of CGRP. All these compounds are considered to be equivalents of the claimed peptide.

Another aspect of the present invention is the use of a drug which possesses the ability to upregulate the biological half-life of CGRP or of a related peptide, and consequently increases the effectiveness of the peptide in terms of bronchoprotector and/or anti-inflammatory properties. The expression "upregulate the biological half-life" is intended to include any intervention, mechanism or drug which increases the bioavailability and duration of action of CGRP. The increase in bioavailibility can be induced either by drugs or compounds that can increase the synthesis, production and release of CGRP in the lung, or by drugs or compounds that prevent its biodegradation, such as inhibitors of endopeptidases. Examples of interventions that may help to increase the synthesis, production and release of CGRP are, but are not limited to, stimulation by specific compounds (such as histamine, bradykinin, interleukins etc) of the sensory nerves and/or neuroendocrine cells in which CGRP is produced, and introduction of DNA constructs which encode all or part of the CGRP protein and a sequence which enhances the transcription of the CGRP gene.

Although the human or mammalian CGRP precursor has not been shown to have CGRP activity, it nevertheless represents a valuable compound. It may well prove to be the case that if the precursor is administered to a mammal, it will be processed in vivo into CGRP subsequently. In any case, the CGRP precursor may be processed in vitro by exposing it to a human or mammalian tissue extract containing processing enzymes.

In the case where the microenvironment affects the biological activity of CGRP or its related homologs and derivatives, addition of drugs may protect the peptide against its loss in biological activity and ultimately improve the capability of CGRP to exert its bronchoprotector and/or anti-inflammatory effects. Specific experimental and physiological conditions have been found to alter the biological half-life of CGRP. For example, inflamed tissues are characterized by an increase in the activity of several endoproteases which are produced either in tissue or are derived from blood circulation and which degrade several endogenous neuropeptides, including CGRP. Over-expression of such enzymatic activities result in changes (i.e., decreases) in tissue response to the peptides. CGRP is very unstable against the action of some endopeptidases, particularly chymases and tryptases which, amongst others, are released from mast cells after an allergen challenge. Thus, examples of drugs that may be used to increase the bioavailibility and duration of action of CGRP primarily include inhibitors of chymases and tryptases as well as inhibitors of any other enzymes (i.e. proteases) which possess the ability to hydrolyse CGRP. As mentioned above, the introduction of different substituents in the amino acid sequence of the peptide may result in increased bioavailability and bioactivity due to specific structural features of the peptide that make it resistant to enzymatic hydrolysis. All of these compounds are also considered to be within the scope of the present invention.

Although only certain embodiments of the invention have been described here in detail with regard to the bioavailibility and the effectiveness of CGRP, it will be apparent to those of skill in the art that other specific interventions may be practiced in order to activate the production and the release of CGRP, to increase its biological half-life or to stimulate the processing of the CGRP precursor, and are all within the spirit of the invention and the scope of the appended claims.

CGRP and other compounds of the present invention are commercially available but may readily be prepared by well-known procedures from known starting materials and intermediates. The desired starting materials and intermediates can be prepared from readily available materials using standard organic reactions, or alternatively, some starting materials and intermediates may be purchased from chemical supply companies. Procedures used to produce CGRP and other compounds of the present invention include, but are not limited to, solid phase synthesis, fragment condensation, classical solution addition, and/or recombinant DNA techniques which may be used for large-scale production.

CGRP and other compounds of the present invention may be employed alone or in conjunction with pharmaceutically non-toxic acceptable salts to form an active pharmaceutical composition. The active agents may also be dispersed in pharmaceutically-acceptable liquid or solid carriers, the proportion of which is determined by the solubility and chemical natures of the peptide and the carriers, the chosen route of administration and standard pharmaceutical practice. The pharmaceutical compositions are administered in an amount effective for the prophylaxis or alleviation of a specific indication or indications.

When used for preventing or alleviating bronchospastic airway responses and lung inflammatory reactions such as those encountered in asthma, the active agents are preferably administered by contacting the subject's respiratory epithelia by causing the subject to inhale breathable particles (i.e. liquid particles or solid particles in the form of an aerosol) comprised of the active agents. Such aerosol administration can be in the form of a nebulized saline solution. Although other routes of administration might also be employed when preventing and alleviating this condition, including oral administration (i.e. tablets or capsules) and parenteral administration (i.e. intravenous injection, subcutaneous injection and intramuscular injection etc), they may be disadvantageous because higher dosages would be required, and this could result in undesirable cardiovascular side effects. Delivery via a nebulized saline solution is preferable because it is contemplated that the present invention will be most useful in a preventative manner or for relief via self-administration. Alternatively, patients using ventilating equipment can be given a breathable dose by converting the liquid and/or solid composition into an aerosol and introducing the aerosol into the inspiratory gas stream of the ventilating apparatus. As noted above, a nebulized aerosol composition can be made using 0.9% saline as the carrier for CGRP to be delivered through inhalation. Suitable solubilizers and other presently known components for aerosol compositions can be used if necessary or desired.

The peptides should be at least about 95% pure and preferably should have a purity of at least 98% when administered to humans. The peptides should be administered under the guidance of a physician and pharmaceutical compositions will usually contain the peptide in conjunction with conventional, pharmaceutically acceptable diluents or carriers which may vary depending upon the form of administration. In general, the compositions are administered in an amount of at least about 0.1 mg. In most cases, doses range from about 0.1 to 1.0 mg. It will be appreciated that optimum dosage will be determined by standard methods for each treatment modality (i.e. age, weight, etc) and conditions (i.e. the particular disorder or disorders being treated) taking into account the indication, its severity, the duration of desired treatment, the route of administration, complicating conditions and the like.

Having now described the invention, the same will be more readily understood by reference to the following examples which are provided by way of illustration. While these examples illustrate specific aspects of the invention, they do not circumscribe the scope of the disclosed invention. It is clear that the invention may be practiced otherwise than as particularly described in the foregoing description and examples. Modifications and variations of the present invention are possible in light of the above teachings and therefore are within the scope of the appended claims.

EXAMPLE 1

Inhibitory Effect of Exogenously Applied CGRP on Agonist-induced Contractile Response in Isolated Airways Adult Hartley albino guinea pigs of either sex, weighing 200–250 g were actively sensitized to ovalbumin (OA), as described in (20). They were injected with 100 mg i.p. and 100 mg s.c. of OA on day 1 and a further 10 mg i.p. was administered as a booster on day 8. They were used experimentally 14 or 15 days later. Control animals received the vehicle solution only. All research protocols conform to the guiding principles for animal experimentation and were approved by the Ethical Committee on Animal Research of the Medical School of the Université de Sherbrooke.

Guinea pigs were killed by exsanguination following intraperitoneal injection of pentobarbitone sodium (50 mg/kg). The trachea and lungs were quickly removed and placed in cold Krebs solution. Both right and left main bronchi were dissected out and cut into spirals. Parenchymal strips (approximately 15 mm×3 mm×3 mm) were cut from the periphery of either right or left lower lobes of the lung as previously described (4, 20). Each preparation was mounted in a 5 ml organ bath containing Krebs solution (37° C.) bubbled with 5% $CO_2$ in $O_2$. Contractions were measured isometrically with a Grass FT03 force displacement transducer and recorded on a Grass polygraph (Model 7D) as tension changes (g). All tissues were subjected to an initial loading tension of 1 g and allowed to equilibrate for 60 min (with changes of bath medium every 15 min) before experimentation began.

The inhibitory effect of CGRP on SP-induced contractions was investigated essentially as described previously (4, 20). Each tissue preparation was first primed with a concentration of carbamylcholine ($10^{-6}$M) to evaluate its responsiveness. When the basal tone was reestablished (after a few washouts), contractions to SP ($5\times10^{-8}$M) were elicited at 15 min intervals with a drug contact time just sufficient to record the peak response. CGRP ($10^{-9}$M to $10^{-6}$M) was then added to the organ bath and 5 minutes later a further spasmogen challenge occurred. The contraction produced in the presence of CGRP was then compared with the mean of two control responses to SP observed prior to CGRP administration. A further concentration of CGRP was tested only when responses to SP showed no further recovery. Concentrations of CGRP were tested in a random order in each experiment. It is worthy of note that the inhibitory effect of CGRP on contractions induced by SP was also examined at a dose of SP ($5\times10^{-8}$M) that induced similar maximal responses in tissues obtained from each group of animals.

Exogenously applied CGRP produces no relaxant and no contractile action per se in guinea pig isolated airways. However, behind this apparent lack of pharmacological activity, CGRP presented a marked ability to prevent agonist induced bronchoconstriction. As illustrated in FIG. 1, pre-incubation of parenchymal strips with CGRP ($10^{-8}$M) caused a slight reduction of SP-induced contraction in control tissues but did not alter the amplitude or the shape of the SP-evoked response in parenchyma from OA-sensitized animals. Pretreatment with higher concentrations of CGRP (i.e. $10^{-6}$M) significantly inhibited the contractions induced by SP in both groups of tissue, the protective effect of CGRP being more marked in parenchymal strips obtained from non-sensitized guinea pigs. Similar results were obtained in isolated bronchi, CGRP being more prone to prevent SP-induced response in control than in OA-sensitized tissues (not shown).

Figure 2:
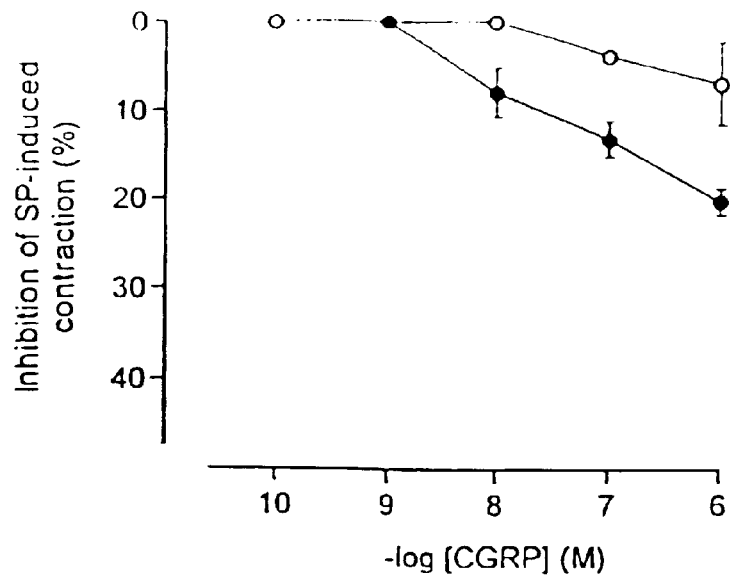
FIG. 2 shows the concentration-dependent inhibition of responses to substance P (SP: $5 \times 10^{-8}M$) by CGRP in guinea pig isolated (A) bronchi and (B) parenchymal strips. CGRP was added in a manner similar to that described in the legend to FIG. 1. Ordinate scale: degree of inhibition produced by CGRP expressed as a percentage of contraction developed by SP alone. Abscissa scale: concentration of CGRP. Each point and bar represents the mean ±SEM of data from 3 to 7 tissues. Solid lines: airways from control (●) and OA-sensitized (○) guinea pigs. Asterisks: significantly different ($p<0.05$) from control.
Figure 2:
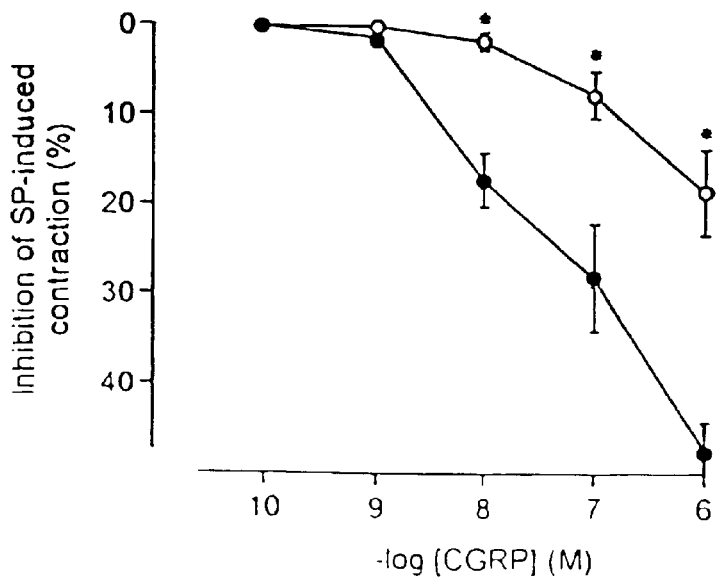

Expressed in terms of percentage of contraction developed by SP alone, CGRP ($10^{10}$ to $10^{6}$M) inhibited contractions of control airways in a concentration-dependent manner (FIG. 2). The antibronchoconstrictor effect of CGRP was however more marked in lower segments of the tracheobronchial tree and at a concentration of $10^{-6}$M, reached an inhibitory effect of 47.3±3% (n=4) in the parenchymal strips and 20.3±1.5% (n=3) in the main bronchus. Similar concentration-dependent inhibitory effects of CGRP were observed in parenchymal strips obtained from OA-sensitized guinea pigs except that the maximum inhibition elicited by $10^{-6}$M of CGRP reached only 18.7±4.8% (n=5). Moreover, CGRP failed to significantly prevent the SP-induced bronchoconstriction in the main bronchi from these same animals (FIG. 2).

Morphometric analysis revealed that tissues obtained from OA-sensitized guinea pigs were specifically characterized by the presence of a clear and marked inflammatory reaction (not shown). Thus, the acute bronchoprotector effect of CGRP, as observed in guinea pig airways, is strongly attenuated in inflammatory conditions.

Figure 3:
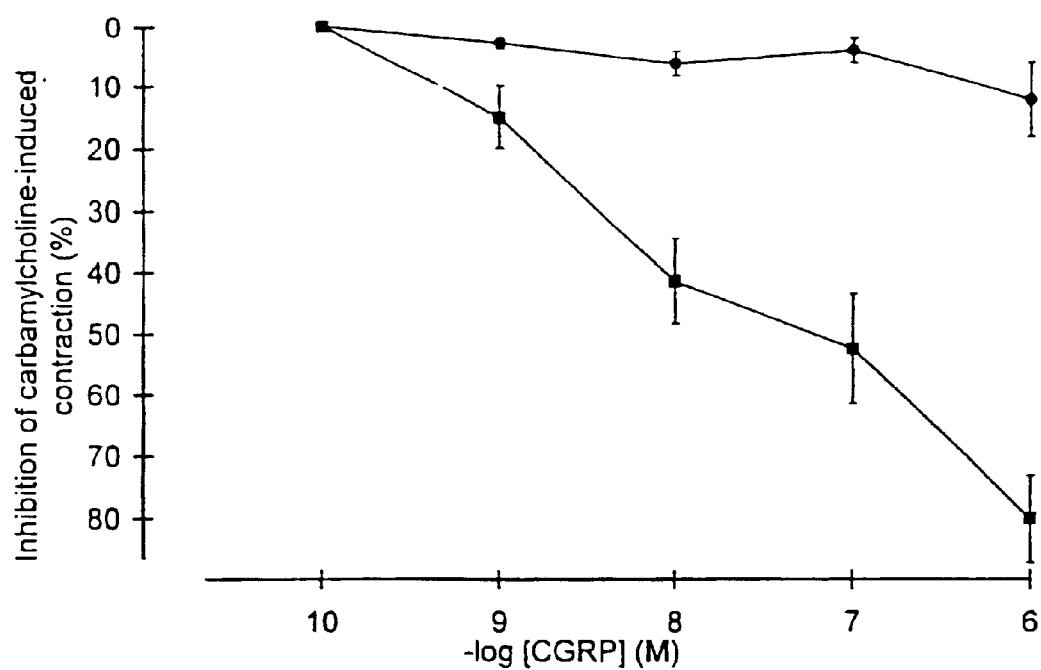
FIG. 3 shows the concentration-dependent inhibition of responses to carbamylcholine ($10^{-6}$M) by CGRP in human isolated airways showing an absence (■) or a presence (●) of strong inflammatory reactions in their mucosa and submucosa. CGRP was added in a manner similar to that described in the legend to FIG. 1. Ordinate scale: degree of inhibition produced by CGRP expressed as percentage of contraction developed by carbamylcholine alone. Abcissa scale: concentration of CGRP. Each point and bar represents the mean ±SEM of data from 3 to 7 tissues. Note that the bronchoprotector effect of CGRP was totally abolished in airways showing marked inflammatory reaction.

Because lung inflammation is a common feature in asthmatic patients, experiments were then repeated using human isolated airways to determine whether this same phenomenon also occurred. Macroscopically normal lung specimens were obtained from 6 patients undergoing surgery for carcinoma and from autopsy (n=9) performed within 6 hours of death. The study protocol was approved by the Ethical Committee of the University Hospital. The ages of the subjects (all males) ranged from 17 to 88 years (mean ±s.e.m.: 57.4±5.1 yr) and none had a known history of either asthma or atopy. The lung specimens were transported to the laboratory in ice-cold pre-oxygenated Krebs solution. Suitable cartilaginous bronchi (internal diameter 2 to 4 mm) were dissected free of adjacent tissue and were either used immediately (autopsy cases) or after 24 hr storage in pre-oxygenated Krebs solution at 4° C. Isolated bronchi were cut into helical strips and set up for isometric recording (initial tension: 1 g) under the conditions described for the isolated guinea pig airways. They were primed by adding $10^{-3}$M carbamylcholine followed by washouts, which ensured a stable function for the rest of the experiment. The protocol for the administration of compounds was the same as that used in the animal airway experiments except that the agonist used to elicit contractions was carbamylcholine ($10^{-6}$M) instead of SP, the latter being much less potent than the cholinergic agonist in human airways. As previously reported, our preliminary data revealed that tissue obtained from autopsy show no differences in their responses to drugs from those obtained surgically. A 24-hour storage does not affect agonist response either. While CGRP did act as an efficient antispasmogenic agent in control tissues, its bronchoprotector properties were totally abolished in inflamed human airways (FIG. 3).

EXAMPLE 2

Inhibitory Effect of Intravenously Administered CGRP on Bronchospasms Induced by Substance P or by Allergen Challenge in Guinea Pigs Guinea pigs were anaesthetized with xylazine (20 mg/kg, i.m.) and ketamine hydrochloride (130 mg/kg, i.m.). The jugular vein and trachea were cannulated and animals were mechanically ventilated with a constant-volume rodent respirator (Havard, model 683) delivering a tidal volume of 5.5 ml/kg at a frequency of 60 cycles/min via the tracheal cannula. Airway resistance was measured by the overflow technique according to well-validated and standardized procedures. Briefly, ventilation overflow (i.e., the pulmonary insufflation pressure or PIP), was recorded at the side arm of the tracheal cannula by means of a differential pressure transducer (Gould P23 ID) connected to a Grass polygraph (model 7D). Airway responsiveness was assessed by measuring the changes in PIP following i.v. injections of the agonists. Changes in PIP, which were taken as an index of changed airway resistance, were measured and expressed in mm of mercury (mm Hg). Each agonist was injected through the jugular vein cannula in a volume of 100 μl followed by a washout with 200 μl of heparinized-saline (100 units/ml).

Before starting the experiment, guinea pig airway responsiveness was first tested by a single i.v. administration of 25 μg/kg of acetylcholine. Based on preliminary experiments, this resulted in an airway constriction which averaged 28.6±1.5 (n=36) and 24.0±1.0 mm Hg (n=38) in control arid OA-sensitized animals, respectively. Only guinea pigs (control and OA-sensitized) showing a reasonably strong (>20 mm Hg) airway constriction to the cholinergic agonist were used in this study. Thereafter, substance P (SP) which was used as the main non-specific spasmogen, was injected intravenously every 20 minutes to induce bronchoconstriction. Care was taken to choose a dose of SP (13.5 µg/kg) so that the same extent of airway constriction could be induced in both animal groups. SP (13.5 µg/kg) was then administered repeatedly (approximately 3 times) until a reproducible constriction (control response) was obtained. After two SP-induced bronchoconstrictions of similar amplitude, CGRP (0.38–114 µg/kg) was administered 5 minutes before a further challenge with SP and the SP challenge was then repeated. The resulting constriction was compared with the control response i.e. the mean of the two pre-inhibition bronchoconstrictions.

To determine the effect of CGRP on antigen-induced challenge in allergic guinea pigs, CGRP (3.8 to 114 mg/kg) was administered intravenously 5 minutes prior to the ovalbumin challenge (0.1 mg/kg, i.v.). The resulting increase in PIP (bronchoconstriction) was compared to responses obtained in control animals i.e. in allergic guinea pigs, which received only saline solution 5 minutes before the i.v. injection of ovalbumin. In some experiments, systemic arterial blood pressure was monitored at the same time via a polyethylene catheter filled with heparinized-saline inserted into a carotid artery and linked to a pressure transducer (Gould P23 1 D) and a Grass polygraph.

Figure 4:
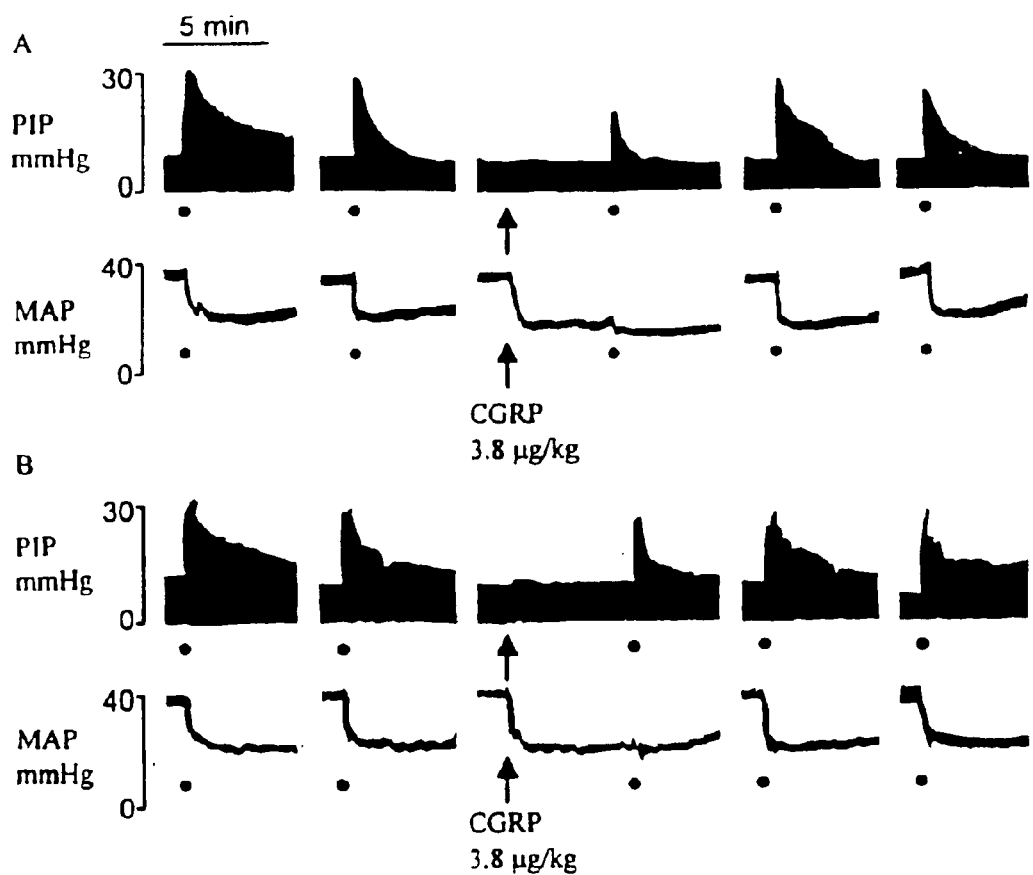
FIG. 4 shows that intravenous injection of CGRP (3.8 mg/kg) does not, by itself, affect baseline airway resistance (pulmonary insufflation pressure: PIP) but potently inhibits the response to Substance P (SP) in both control (A) and OA-sensitized (B) guinea pigs. Bronchospasms were induced with 13.5 mg/kg of SP (●) every 20 minutes before and after the bolus administration of CGRP. Ordinate scale: changes of PIP and MAP in mmHg. Abscissa scale: time in minutes.
Figure 5:
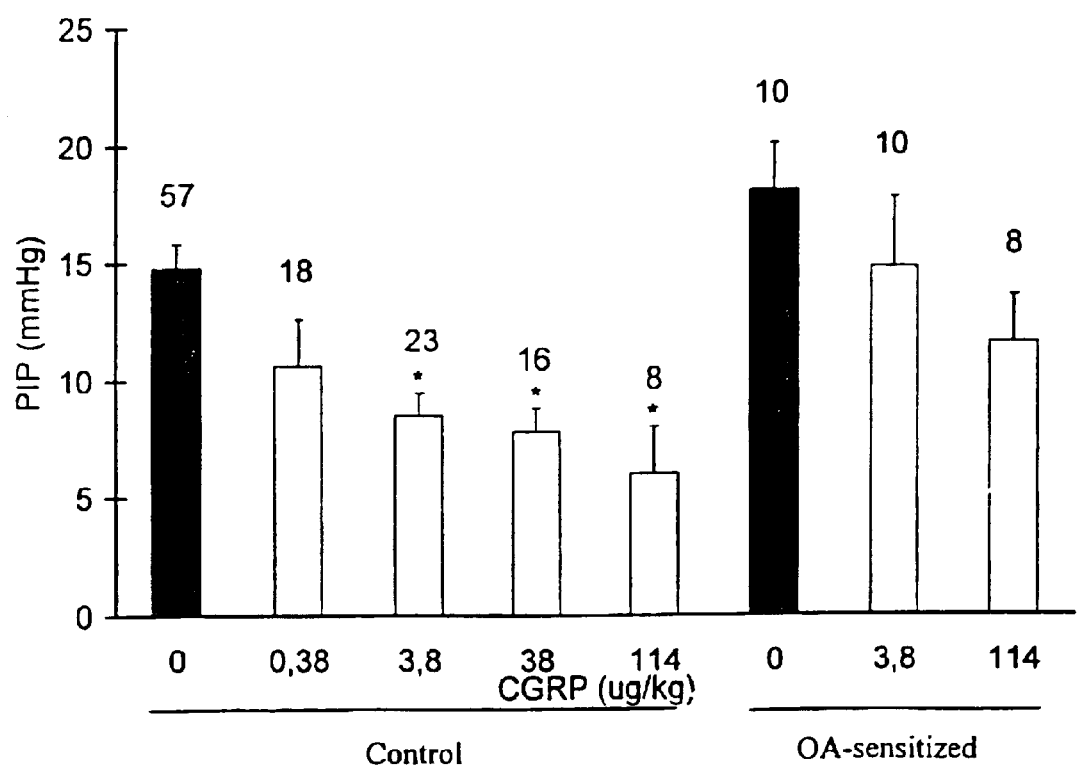
FIG. 5 is the dose response curve for CGRP protection against substance P-induced increases in airway resistance (PIP: mmHg) in control and OA-sensitized guinea pigs. Each column and bar represents the mean ±standard error of the mean (S.E.M.) of data obtained from 8 to 57 animals (numbers given on top of columns). CGRP (0.38 to 114 mg/kg) was injected 5 minutes prior to the administration of SP (13.5 mg/kg) as described in the legend to FIG. 4. Asterisks: significantly different ($p<0.05$) from SP injection without a pre-administration of CGRP (filled columns).

Measurement of airway resistance is a more natural reflection of airway response following chemical or allergen stimuli. As shown in FIG. 4, intravenous administration of CGRP (3.8 mg/kg) did not affect baseline airway resistance by itself, but potently inhibited the response to SP (13.5 mg/kg) in non-sensitized animals. In contrast, CGRP (3.8 mg/kg) failed to significantly prevent the SP-induced increase in airway constriction in OA-sensitized guinea pigs. The protective effects of increasing doses of CGRP on airway constriction induced by SP in both control and OA-sensitized guinea pigs are illustrated in FIG. 5. When added 5 minutes before SP, CGRP (0.38 to 114 mg/kg) prevented bronchoconstriction in a dose-related manner in control animals, providing a 60% inhibition at the highest dose used in these experiments. In contrast, the protective effect of CGRP on SP-induced airway constriction was deeply attenuated in OA-sensitized animals. At 114 mg/kg, the inhibition provided by CGRP reached only 36%, which means a reduction by more than 40% in its capability to exert its bronchoprotective action. It is worth noting that the impaired capability of intravenously administered CGRP to exert its bronchoprotector effect in OA-exposed animals was of similar magnitude (reduction by more than 40%) as that observed in experiments carried-out in isolated airways (FIG. 2). Thus, even though intravenously administered CGRP can reach its receptor sites in the lung and exert its bronchoprotector properties on exogenous agonist SP-induced increase in airway resistance, its efficiency may be markedly impaired in inflammatory conditions. Since we have already shown that CGRP is released from the lung following an allergen challenge (unpublished data), these results reveal that the hyperreactive state of the airways that characterize the asthmatic condition could be associated with a loss in the overall capability of CGRP to exert its bronchoprotective action.

Figure 6:
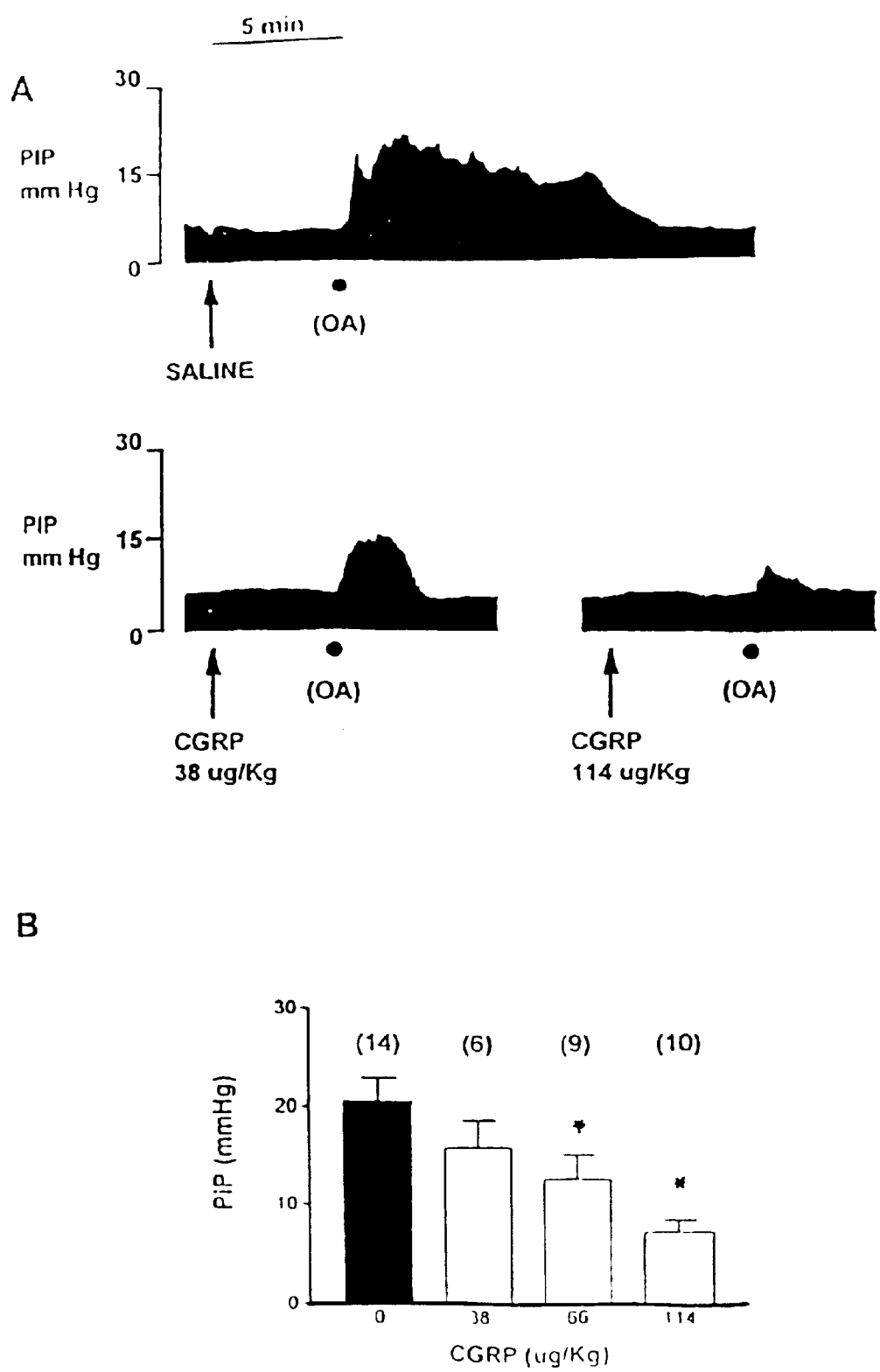
FIG. 6 shows that intravenous injection of CGRP blocks allergen-induced increases in airway resistance (PIP: mm Hg) in asthmatic guinea pigs. PIP values after ovalbumin challenge (OA, 0.25 mg/kg, i.v.) were compared to baseline. A: OA challenge was performed either in the absence (saline) or in the presence of various doses of CGRP. Ordinate scale: changes of PIP in mmHg. Abcissa scale: time in minutes. B: CGRP pretreatment (0.38 to 114 mg/kg; 5 min before the allergen challenge) prevented, in a dose-related manner, the allergen-induced bronchospasm seen when guinea pigs were not pretreated. Values are mean ±SEM for 6 to 14 animals. Asterisks: significantly different ($p<0.05$) from allergen-induced increase in airway resistance without a pre-administration of CGRP (filled columns).

Analysis of the effects of CGRP on allergen-induced bronchospasms in allergic guinea pigs reveals some other interesting aspects of the natural properties of this peptide. As shown in FIG. 6 A, i.v. administration of 0.25 mg/kg of OA in allergic guinea pigs resulted in an increase in airway resistance (PIP) which averaged 25.1±2.0 mm Hg (n=23). While saline administration 5 minutes before the injection of OA had no effect on the magnitude of the response induced by the allergen challenge, CGRP pretreatment (3.8 to 114 mg/kg) inhibited in a dose-related manner (B) the OA-induced increase in airway resistance. These results indicate that provided that the concentration of CGRP remains sufficiently high in the blood circulation (i.e. that its bioavailability is being maintained and/or increased), it can reach its receptor sites located in the lungs in a relatively quite active state and still maintain its specific bronchoprotector properties, even in the presence of lung inflammatory conditions. Thus, the bronchospasms induced by an allergen challenge can be alleviated with the administration of active CGRP.

A similar bronchoprotector effect on allergen-induced bronchospasms in allergic guinea pigs was observed with adrenomedullin (a natural homolog of CGRP) as well as with the linear analog of CGRP diacetoamidomethyl cysteine CGRP([Cys(ACM)$^{2,7}$]CGRP) (not shown). This indicates that these peptides may also be valuable to prevent asthma bronchospasms.

EXAMPLE 3

Effect of Inhaled CGRP on Eosinophil Chemotaxis in Airways of Allergic Guinea Pigs Guinea pigs were actively sensitized to ovalbumin as described above. On the days of experimentation, they were challenged by inhalation (3 min) of aerosolized ovalbumin (1.5 mg/ml). Fifteen minutes after the ovalbumin challenge, an aerosol solution of 30 µg/ml CGRP or sterile 0.9% saline solution (control) was inhaled for 10 minutes in only one dosage regime. Ovalbumin and CGRP for inhalation were dissolved in sterile 0.9% saline solution and converted into an aerosol with a portable nebulizer driven by compressed air at 7 L/min. After 24 hrs, animals were divided equally into different groups and cellular infiltration into the airways was assessed by both cytological and histopathological examinations.

Guinea pigs were anesthetized with pentobarbitone sodium, 50 mg/kg injected intraperitoneally and exsanguinated by dorsal aorta section. Bronchoalveolar lavage (BAL) was performed with 4×5 ml volumes of phosphate buffered saline (PBS) solution at 37° C. The recovered fluid was combined and the cells were pelleted by centrifugation at 1250 rpm for 10 min at 4° C. After resuspension in 1 ml of PBS, total leucocyte counts, were done with a Newbauer hemocytometer. Differential cell counts were performed on cytospin preparations stained with 5% Giemsa. Standard morphologic criteria were used to identify the population of eosinophils.

For histopathological examination of the lungs, guinea pigs were euthanized as described above. Samples of lungs were removed and fixed in Bouin's solution. After the fixation, the specimens were embedded in paraffin wax, cut into 5 mm thick sections and stained with hematoxylineosin.

When aiming to achieve asthma control, several major determinants of the disease need to be targeted. Asthma symptoms are mainly caused by variable airway obstruction. The variability of the airway obstruction can be ascribed to airway hyperresponsiveness, which is characterized not only by increased sensitivity but also by an exaggerated contraction of the airway in response to a range of non-specific irritants. The underlying causes of airway hyperresponsiveness are not quite clear at present but there is a concensus that airway inflammation probably paves the way to such condition. Thus, in addition to exerting a bronchoprotective effect, an ideal asthma drug should also effectively suppress and/or reduce airway inflammation in asthmatic airways. Such potential effect for CGRP was tested in allergic guinea pigs.

Figure 7:
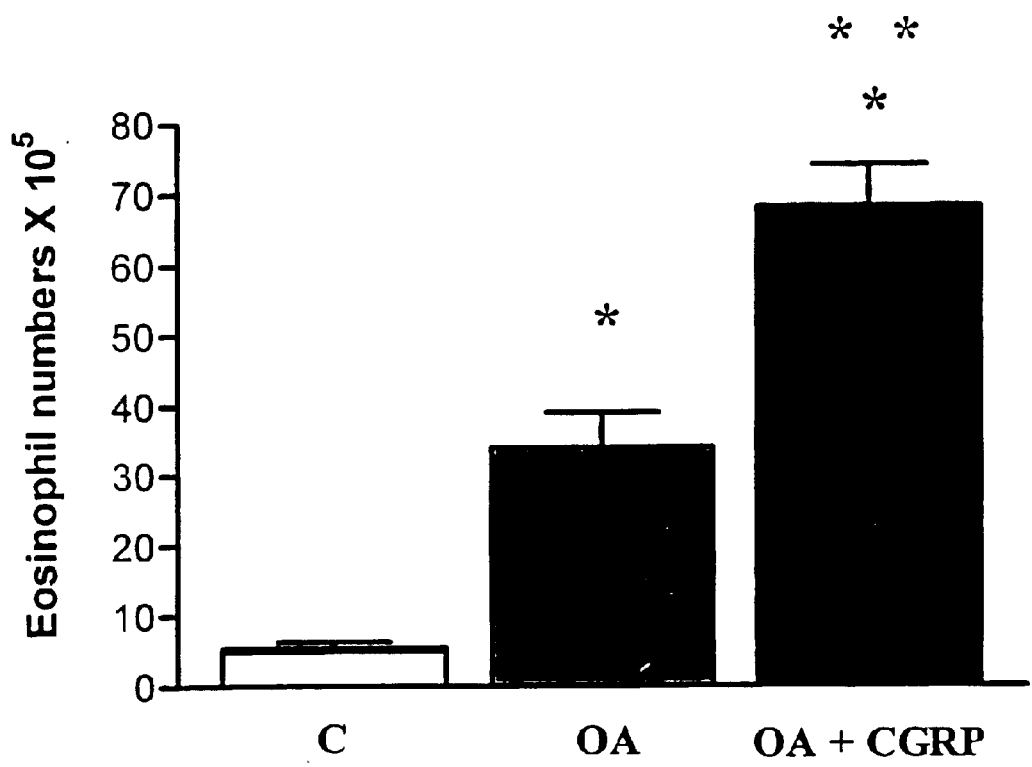
FIG. 7 shows that in allergic guinea pigs, a single inhalation treatment with CGRP, 15 minutes after the ovalbumin challenge, causes a significant increase in the recruitment of eosinophils in the bronchoalveolar lavage (column: OA+CGRP), a phenomenon which is accompanied by a drastic reduction in the population of these cells in the lung tissues (not shown). Values are mean ±SEM for 6 to 9 animals per group. * $p<0.05$ versus control. ** $p<0.05$ versus OA in the absence of CGRP.

As illustrated in FIG. 7, only a small number of eosinophils ($5.4 \pm 0.9 \times 10^5$ cells/10 ml BAL; n=6) are found in the BAL of OA-sensitized guinea pigs (column C). Similarly, few eosinophilic cells are detected in the bronchial walls of these animals (not shown). BAL eosinophil number rose 6-fold from baseline 24 hours after OA-provocation (column OA), a phenomenon which was accompanied by a significant increase in the rate of eosinophil infiltration in bronchial mucosa (not shown). When inhaled 15 minutes after OA-challenge, CGRP further increased the rise in BAL-eosinophil numbers observed at 24 hours (by 2 fold versus OA and 12 fold versus control) (column: OA+CGRP), but drastically decreased the population of eosinophils in lung tissues (not shown). This suggests that inhaled CGRP can induce/activate either directly or indirectly eosinophil chemotaxis in such a way that it can reduce their stay in the bronchial mucosa, and consequently their toxic and harmful effects.

EXAMPLE 4

Effect of Inhaled CGRP on Bronchospasm Induced by Non-specific Bronchoprovocation (Metacholine) or by Allergen Challenge in Sheep Eighteen sheep with a mean weight of 35 kg (range: 24 to 52 kg) were used for this study. All had a chronic carotid loop to facilitate measurements of mean arterial blood pressure and heart rate. Ten of these animals were defined as non-allergic and 8 as allergic, based on the absence or presence of both early and late airway responses after a standard inhalation challenge with *Ascaris suum* antigen. All sheep were allowed a 4-week recovery period after the allergen challenge before experimentation began. For each of the procedures hereafter presented, the unsedated animals were restrained on a standard shopping cart in the prone position and their heads were immobilized. After topical anesthesia of the nasal passages with 2% lidocaine solution, a balloon catheter was advanced through one nostril into the lower esophagus. Subsequently, a cuffed nasotracheal tube (7 to 8 mm in diameter) was placed with the guidance of a flexible fiberoptic bronchoscope.

The techniques used for investigating airway mechanics were again well-validated and standardized procedures (as is usually the case with large mammals). Briefly, pleural pressure was estimated via the esophageal balloon catheter (filled with 1 ml of air), which was positioned 5 to 10 cm from the gastroesophageal junction. In this position, the end expiratory pleural pressure ranged between −2 and −5 cm $H_2O$ in different animals. Lateral pressure in the trachea was measured with a sidehole catheter (inner diameter=2.5 mm) advanced through and positioned distal to the tip of the endotracheal tube. Transpulmonary pressure which was defined as the tracheal pressure minus pleural pressure was measured with a differential pressure transducer (Hewlett-Packard 270, Palo Alto, Calif.) catheter system that showed no change in amplitude as phase shift between pressure and flow to a frequency of 6 Hz. For the measurement of pulmonary resistance (RL), the proximal end of the endotracheal tube was connected to a pneumotachograph (Fleisch No.1; Collins, Mass. U.S.A.), and the volume signal was electrically differentiated to obtain flow. The transpulmonary pressure and flow signals were recorded on a Hewlett Packard (model 7754B, Mass. USA) multichannel recorder, which was linked to a PC 386 Personal Computer (IBM Equipment, Montreal, Quebec) for online calculation of mean $R_L$ by dividing the change in transpulmonary pressure by the change in flow at mid-tidal volume ($V_t$) (obtained by digital integration). Analysis of at least eight consecutive breaths, free of swallowing artifact, was used to determine RL in cm $H_2O$/L/sec. Immediately after measuring RL, thoracic gas volume (Vtg) was measured in a constant-volume body plethysmograph to obtain specific lung resistance ($SR_L = R_L \times Vtg$) in L×cm $H_2O$/L/sec.

All aerosols were generated using a disposable medical nebulizer (Raindrop, Puritan-Bennett, Lenexa, Kan.) which produced an aerosol with a mass median aerodynamic diameter of 3.6 mm (geometric S.D. 1.9), as determined by a seven stage Andersen cascade impactor (Andersen, Inc. Atlanta, Ga.). The output of the nebulizer was directed into a plastic T-piece, one end of which was attached to the endotracheal tube and the other end of which was connected to the inspiratory port of a BENNETT MA-1 respirator (Puritan Bennett Corp., Los Angeles, Calif.). To control the aerosol delivery, a dosimeter system was used, consisting of solenoid valve and a source of compressed air (20 psi) which was activated for 1 sec at the beginning of the inspiratory cycle of the Puritan BENNETT respirator system. All aerosols were delivered at a tidal volume of 500 ml and a rate of 20 breaths per minute.

Agents were prepared as follows. Ascaris suum extract (Greer Diagnostic, Lenoir, N.C.) was diluted with phosphate buffered saline (PBS) to a concentration of 82,000 protein nitrogen units/ml and delivered as an aerosol over 20 minutes (=400 breaths). Metacholine (Sigma Chemical Co, St-Louis, Mo.) was dissolved in PBS at concentrations of 0.25, 0.5, 1.0, 2.0 and 4.0% wt/vol (2 ml) and delivered as an areosol. The interval between doses was less than 10 minutes. Salbutamol (0.5 mg) and CGRP (0.5 mg) were dissolved in PBS in concentrations of 0.25 mg/ml and delivered as aerosols. Vehicle control for each agent was buffered saline solution (PBS).

To assess airway responsiveness, we performed cumulative doseresponse curves to metacholine by measuring SRL immediately after inhalation of buffer (PBS) and after each consecutive administration of 10 breaths of increasing concentrations of metacholine up to 4% wt/vol. The provocation test was discontinued when SRL increased over 400% from the post saline value, or after the highest metacholine concentration had been administered. Airway responsiveness was determined by calculating the cumulative metacholine dose (in breath units: BU), which increased S,RL by 400% over the postsaline value (PC400) by interpolation from the doseresponse curve. One BU of metacholine was defined as one breath of an aerosol solution containing 1.0% wt/vol metacholine.

After baseline measurements of $SR_L$, sheep (n=8) underwent inhalation challenge with *Ascaris suum* antigen. Measurements of SRL were repeated immediately (i.e. 10 and 30 minutes) after antigen challenge and subsequently at 1, 2, 3, 4, 4.5, 5, 5.5, 6, 6.5 and 7 hours after challenge. These challenges were used to deternine SRL values for untreated animals.

Figure 8:
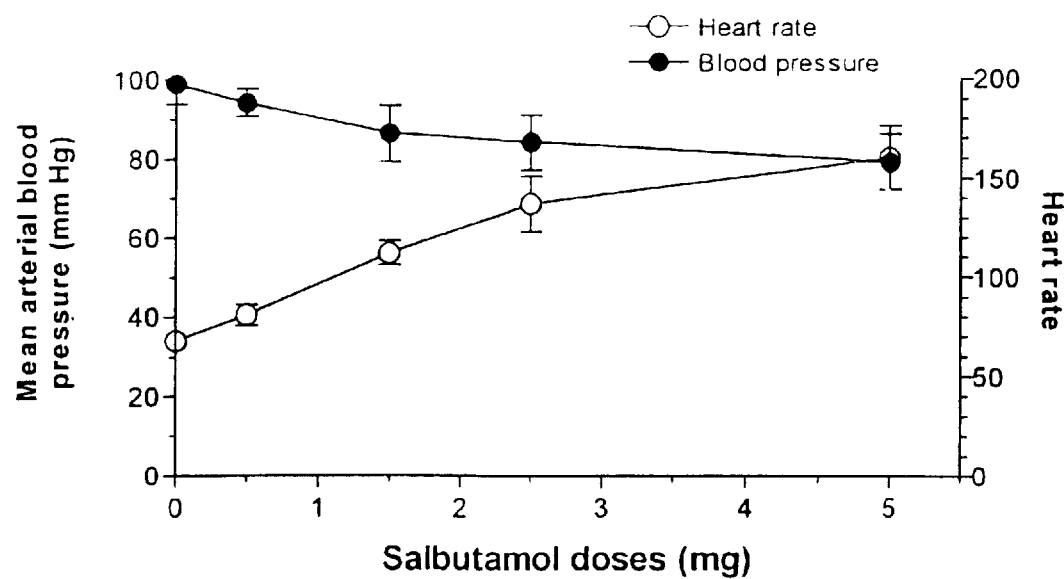
FIG. 8 shows changes in haemodynamic paradigms in asthmatic sheep following inhaled administration of increasing doses of salbutamol or CGRP. It can be noted that while salbutamol (A) induces both hypotension and increase in heart rate, CGRP (B) is without any undesirable side effects on the cardiovascular system. Values are mean ±SEM for 4 animals in each group. Asterisks: significantly different ($p<0.05$) from control i.e., without a pre-administration of salbutamol.
Figure 8:
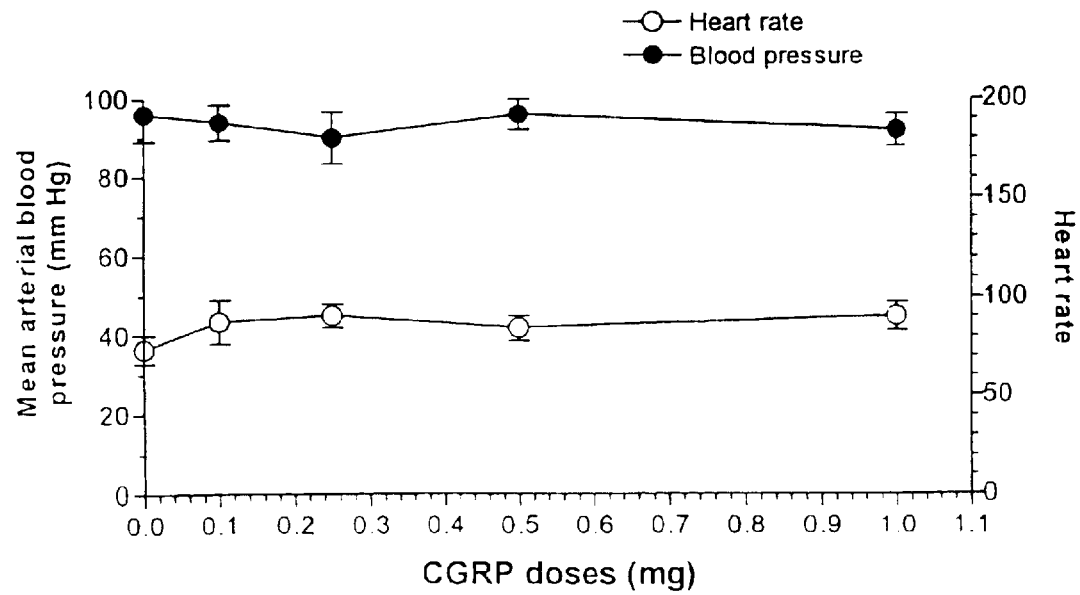

In essence, three experimental protocols were followed for the studies described in this example. In the first experimental protocol, 3 non-allergic and 3 allergic sheep were subjected to an aerosol challenge of increasing concentrations of CGRP (0.1, 0.25, 0.5 and 1.0 mg/2 ml) in PBS and SRL was measured for six hours (every 15 minutes for one hour, then every 30 minutes). Measurements of mean arterial blood pressure (MAP) and heart rate were also performed prior to challenge and at the same time intervals as those for SRL. Measurements of these haemodynamic paradigms were made via a polyethylene catheter filled with heparinized saline inserted into a carotid artery and linked to a pressure transducer (Gould P231D) and a Grass polygraph. Since CGRP inhalation appeared to be without any significant effect on these parameters (these results are illustrated in FIG. 8), two additional protocols were subsequently incorporated into our studies in order to determine A) whether CGRP inhalation could prevent non-specific airway responsiveness induced by metacholine provocation and B) if CGRP had any bronchoprotective effect with regard to allergen challenge.

To determine the effect of CGRP and salbutamol on non-specific airway responsiveness, baseline measurements of SRL were determined before the sheep were treated with an aerosol of CGRP (0.5 mg; 2 ml total volume) or an aerosol of salbutamol (0.5 mg; 2 ml total volume). After administration of the compound (CGRP or salbutamol) SRL was remeasured and the sheep subsequently underwent a metacholine challenge, as described above.

To determine the effect of CGRP and salbutamol on allergen induced bronchoconstriction, baseline measurements of SRL were determined before the sheep were treated with an aerosol of CGRP (0.5 mg; 2 ml total volume) or an aerosol of salbutamol (0.5 mg; 2 ml total volume). After administration of the compound (CGRP or salbutamol) $SR_L$ was remeasured and the sheep subsequently underwent a challenge with Ascaris suum antigen as described above.

Figure 9:
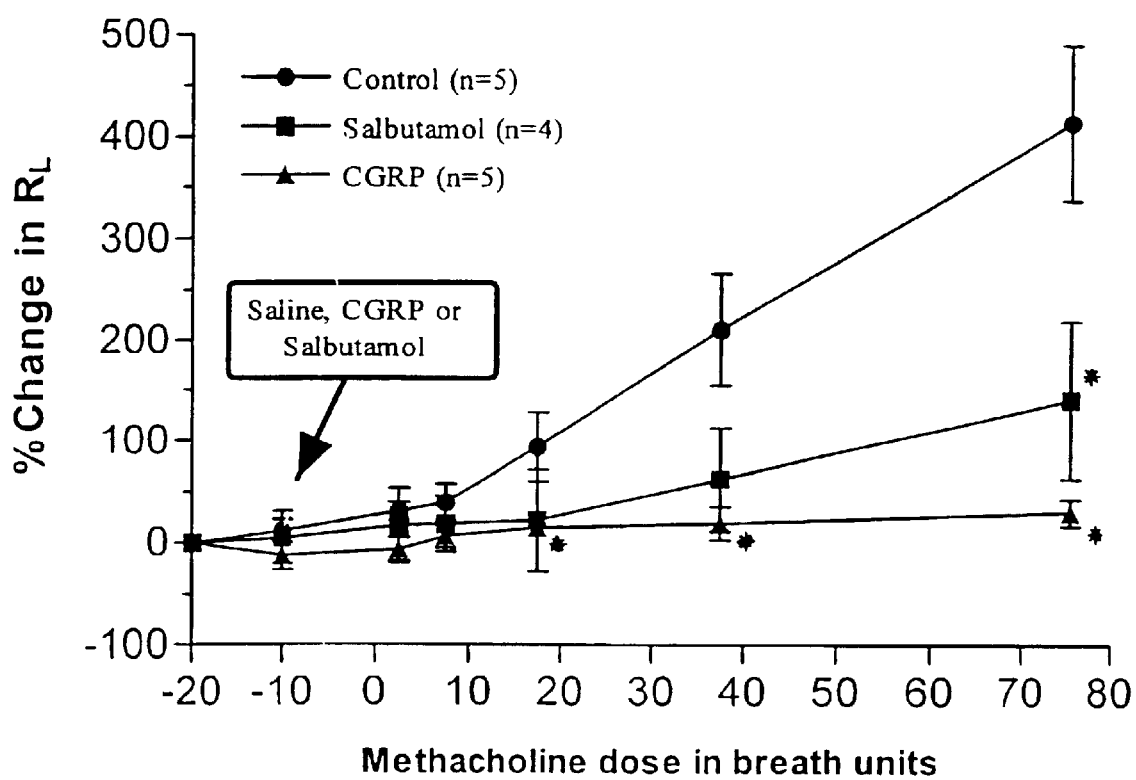
FIG. 9 shows that a single inhalation treatment with CGRP in asthmatic sheep results in a total blockade of non-specific airway hyperresponsiveness induced by methacholine. CGRP pretreatment is more efficient and more potent than salbutamol (a β2 agonist used in the treatment of asthmas to block the increased resistance attribuable to non-specific challenge (metacholine) when compared to saline (control) pretreatment. Values are mean ±SEM. * $p<0.05$ versus control.

The bronchoprotector effects of CGRP on airway responses are more impressive when the peptide is administered by inhalation. Such experiments were carried out in the allergic sheep asthma model. Metacholine provocation was used to demonstrate non-specific airway responsiveness. As shown in FIG. 9, all allergic sheep responded to aerosol metacholine with a dose-dependent increase in pulmonary resistance ($R_L$) with a mean maximal value of 415% (the range being 202 to 652% of baseline). While salbutamol inhalation at a dose of 0.5 mg (in 2 ml of phosphate-buffered saline PBS) provides partial but significant protection (reduction by an average of 65%) against metacholine bronchoprovocation, inhaled CGRP at the same dose of 0.5 mg (in 2 ml PBS) totally prevents (100%) the increase in airway resistance induced by the cholinergic agonist.

Figure 10:
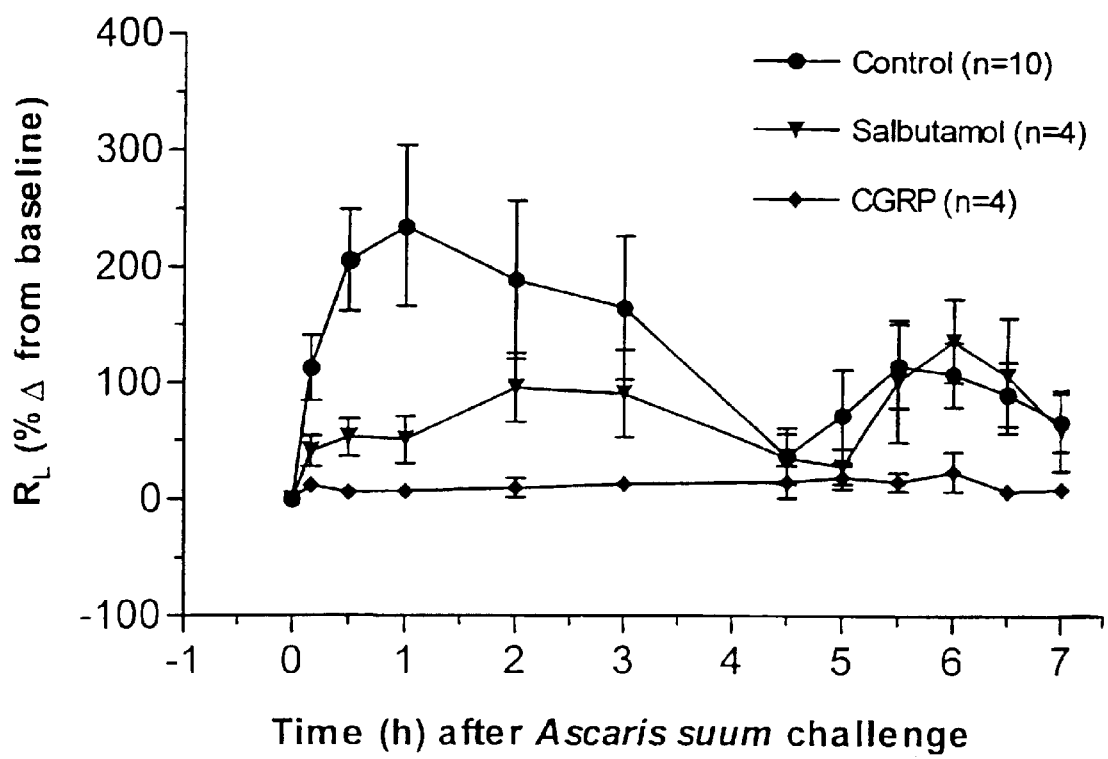
FIG. 10 shows that CGRP inhalation blocks allergen-induced increases in airway resistance in asthmatic sheep. It can be noted that while salbutamol has no effect on the late asthmatic response, CGRP totally blocks both the early-phase (0 to 4 hours) and the late-phase (5 to 7.5 hours) increase in airway resistance attribuable to *Ascaris suum* challenge when compared to saline pretreatment (control). Values are mean ±SEM. * $p<0.05$ versus control.

CGRP pretreatment not only blocks the increase in non-specific airway responsiveness evoked by metacholine provocation but also prevents allergen-induced increases in pulmonary resistance. The pooled results of all eighteen sheep used for these experiments are shown in FIG. 10. Inhalation of Ascaris suum antigen resulted in both early and late bronchial responses characteristic for this model when the sheep were pretreated with placebo (PBS, 2 ml by aerosol; control). Mean RL increased 240% (p<0.05) over baseline within 1 hour after challenge; RL remained significantly elevated 3 hours after challenge but then returned to prechallenge values after 4 hours. By 5.5 hours after antigen challenge, mean RL increased again to 130±25% (p<0.05) over baseline and remained significantly elevated through the remainder of the 7.5-hour observation period. Pretreatment with aerosolized salbutamol (0.5 mg in 2 ml PBS) 20 minutes before antigen challenge slightly reduces (by 45%) the peak of the early phase response but does not affect the late phase bronchoconstriction to Ascaris suum antigen. In contrast, pretreatment with CGRP (0.5 mg in 2 ml of PBS by aerosol) completely blocks both acute and late Ascaris suum-induced increases in RL. As mentioned above (Example 2) similar bronchoprotective effects were also observed by using adrenomedullin or the linear analog of CGRP, namely [Cys(ACM)$^{2,7}$] CGRP. As a result, these and similar peptides, when given by inhalation, may also be particularly valuable for the treatment of bronchial hyperreactivity.

In summary, as illustrated above, CGRP in the context of the present invention is considerably more effective than salbutamol in preventing nonspecific and allergen-induced bronchoconstriction. It has longer-lasting activity than any other known bronchoprotector agent and can completely prevent late-phase responses associated with an allergen challenge. Moreover, when administered by inhalation, CGRP also combines interesting anti-inflammatory properties by decreasing the time of residence for the eosinophils in the bronchial mucosa. In the range of doses required to offer profound symptom relief, this peptide is also devoid of undesirable heamodynamic side effects. All these features and the various other characteristics which have been mentioned throughout this description make CGRP a new, secure and ideal medicament for preventing, reducing and/or alleviating the pathophysiological manifestations associated with asthma.

REFERENCES

1. Barnes, P. J., J. N. Baraniuk, and M. G. Belvisi. 1991. Neuroptides in the respiratory tract: part II. Am. Rev. Respir. Dis. 144:1391–1399.
2. Lundberg, J. M., A. Franco-Cereceda, X. Hua, T. Hokfelt, and J. A. Fischer. 1985. Co-existence of substance P and calcitonin gene-related peptide-like immunoreactivities in sensory nerves in relation to cardiovascular and bronchoconstrictor effects of capsaicin. Eur. J. Pharmacol. 108:315–319.
3. Martling, C. R., A. Saria, J. A. Fischer, T. Hokfelt, and J. M. Lundberg. 1988. Calcitonin gene-related peptide and the lung: neuronal coexistence with substance P, release by capsaicin and vasodilatory effect. Regul. Pept. 20:125–139.
4. Cadieux, A., C. Lanoue, P. Sirois, and J. Barabe. 1990. Carbamylcholine-and 5-hydroxytryptamine-induced contraction in rat isolated airways: inhibition by calcitonin gene-related peptide. Br. J. Pharmacol. 101:193–199.
5. Luts, A., E. Widmark, R. Ekman, B. Waldeck, and F. Sundler, 1990. Neuropeptides in guinea pig trachea: distribution and evidence for the release of CGRP into tracheal lumen. Peptides 11:1211–1216.
6. Bhogal, R., R. L. G. Sheldrick, R. A. Coleman, D. M. Smith, and S. R. Bloom. 1994. The effects of IAPP and CGRP on guinea pig tracheal smooth muscle in vitro. Peptides 15:1243–1247.
7. Pinto., A., K. Sekizawa, M. Yamaya, T. Ohrui, Y. X. Jia, and H. Sasaki. 1996. Effects of adrenomedullin and calcitonin gene-related peptide on airway and pulmonary vascular smooth muscle in guinea pigs. Eur. J. Pharmacol. 119:1477–1483.
8. Hamel, R., and A. W. Ford-Hutchinson, 1988. Contractile activity of calcitonin gene-related peptide on pulmonary tissues. J. Pharm. Pharmacol 40:210–211.
9. Tschirhart, E., C. Bertrand, E. Theodorsson and Y. Landry. 1990. Evidence for the involvement of calcitonin gene-related peptide in the epithelium-dependent contraction of guinea pig trachea in response to capsaicin. Naunyn-Schmied. Arch. Pharmacol. 342:177–181.
10. Gatto, C., R. C. Lussky, L. W. Ericksson, K. J. Berg, J. D. Wobken, and D. E. Johnson. 1989. Calcitonin and CGRP block bombesin- and substance P-induced increases in airway tone. *J. Appl. Physiol.* 66:573–577.
11. Kanazawa, H., T. Kawaguchi, H. Kamoi, T. Fuji, S. Kudoh. K. Hirata, N. Kurihara, and L. Yoshikawa. 1996. Calcitonin gene-related peptide antagonizes the protective effect of adrenomedullin on histamineinduced bronchoconstriction. *Clin. Exp. Pharmacol. Physiol.* 23:472–475.
12. Nagase, T., E. Ohga, H. Katayama, E. Sudo, T. Aoki, T. Matsuse, Y. Ouchi, and Y. Fukuchi. 1996. Roles of calcitonin gene-related peptide (CGRP) in hyperpnea-induced constriction in guinea pigs. *Am. J. Respir. Crit. Care Med.* 154:1551–1556.
13. Kroll, F., J. A. Karlsson, J. M. Lundberg, and C. G. A. Persson. 1990. Capsaicin-induced bronchoconstriction and neuropeptide release in guinea pig perfused lungs. *J. Appl. Physiol.* 68:1679–1687.
14. Kanemura, T., J. Tamaoki, S. Horii, N. Sakai, K. Kobayashi, K. Isono, S. Takeuchi, and T. Takizawa. 1990. Calcitonin gene-related peptide augments parasympathetic contraction of rabbit tracheal smooth muscle in vitro. *Agents Actions* 31: 219–224.
15. Kannan, M. S., and D. E. Johnson. 1991. Functional innervation of pig tracheal smooth muscle: neural and non-neural mechanisms of relaxation. *J. Pharmacol. Exp. Ther.* 260:1180–1184.
16. Martling, C. R., R. Matran, K. Alving, T. Hokfelt, and J. M. Lundberg. 1990. Innervation of lower airways and neuropeptide effects on bronchial and vascular tone in the pig. *Cell. Tiss. Res.* 260:223–233.
17. Manzini, S. 1992. Bronchodilatation by tachykinins and capsaicin in the mouse main bronchus. *Br. J. Pharmacol.* 105:968–972.
18. Parsons, G. H., G. M. Nichol, P. J. Barnes, and K. G. Chung. 1992. Peptide mediator effects on bronchial blood velocity and lung resistance in conscious sheep. *J. Appl Physiol.* 72:1118–1122.
19. Ninomiya, H., Y. Uchida, T. Endo, M. Ohtsuka, A. Nomura, M. Saotome, and S. Hasegawa. 1996. The effects of calcitonin generelated peptide on tracheal smooth muscle of guinea pigs in vitro. *Br. J. Pharmacol.* 119:1341–1346.
20. Cadieux, A. et al. 1999. *Am J. Respir. Crit. Care Med.* 159: 235–243.
21. Cadieux, A. et al, *Proc. APS/ASPET*, p. A60, No. 44.11, 1988.

What is claimed is:

1. A method of reducing a stimulus-induced airway response selected from the group consisting of airway constriction, bronchospasm, airway hyperreactivity, eosinophil accumulation in bronchial walls, an increase in airway resistance, or combinations thereof, said method comprising:

administering by inhalation to a subject at risk of experiencing said stimulus-induced airway response a therapeutically effective amount of an agent selected from the group consisting of:

(a) human calcitonin gene-related peptide (human CGRP);

(b) rat CGRP;

(c) the diacetoamidomethyl cysteine form of (a); and (d) the diacetoamidomethyl cysteine form of (b); wherein said agent is administered prior to said airway response and wherein said method results in no or substantially no haemodynamic side effects.

2. The method of claim 1 wherein said stimulus is selected from the group consisting of a non-specific stimulus and exposure to an irritant.

3. The method of claim 2 wherein said irritant is selected from the group consisting of an allergen and an agonist.

4. The method of claim 1 wherein said airway response is selected from the group consisting of early or late phase responses induced by said stimulus.

5. The method of claim 1 wherein said airway comprises the lower segments of the tracheobronchial tree.

6. The method of claim 1 wherein said agent is selected from the group consisting of human CGRP and rat CGRP.

7. The method of claim 1, wherein said agent is selected from the group consisting of the diacetoamidomethyl cysteine form of human CGRP and the diacetoamidomethyl cysteine form of rat CGRP.

8. The method of claim 1 wherein said agent is selected from the group consisting of human αCGRP and rat αCGRP.

9. The method of claim 1, wherein said agent is selected from the group consisting of the diacetoamidomethyl cysteine form of human αCGRP and the diacetoamidomethyl cysteine form of rat a CGRP.

10. The method of claim 1, wherein said agent is administered such that it contacts the respiratory epithelium of said subject.

11. The method of claim 1, wherein said agent has a purity of at least about 95 to 98%.

12. The method of claim 1, wherein said agent is dispersed within a composition comprising a pharmaceutically acceptable excipient, and/or a liquid or solid carrier.

13. The method of claim 12, wherein said composition is formulated as an aerosol or dry powder.

* * * * *

UNITED STATES PATENT AND TRADEMARK OFFICE
CERTIFICATE OF CORRECTION

PATENT NO.    : 6,743,429 B2
DATED         : June 1, 2004
INVENTOR(S)   : Alain Cadieux It is certified that error appears in the above-identified patent and that said Letters Patent is hereby corrected as shown below:

Title page,
Item [73], Assignee, please delete "Sherbrooke University" and insert
-- Universite de Sherbrooke --.

Signed and Sealed this

Sixteenth Day of November, 2004

JON W. DUDAS
*Director of the United States Patent and Trademark Office*